United States Patent

Murakami

(10) Patent No.: US 10,765,554 B2
(45) Date of Patent: Sep. 8, 2020

(54) PIERCING NEEDLE-EQUIPPED CANNULA

(71) Applicant: MANI, Inc., Utsunomiya-shi, Tochigi (JP)

(72) Inventor: Etsuo Murakami, Utsunomiya (JP)

(73) Assignee: MANI, INC., Utsunomiya-shi, Tochigi (JP)

( * ) Notice: Subject to any disclaimer, the term of this patent is extended or adjusted under 35 U.S.C. 154(b) by 191 days.

(21) Appl. No.: 15/779,526

(22) PCT Filed: Nov. 29, 2016

(86) PCT No.: PCT/JP2016/085359
§ 371 (c)(1),
(2) Date: May 28, 2018

(87) PCT Pub. No.: WO2017/094708
PCT Pub. Date: Jun. 8, 2017

(65) Prior Publication Data
US 2018/0344519 A1 Dec. 6, 2018

(30) Foreign Application Priority Data

Nov. 30, 2015 (JP) ................................. 2015-234105

(51) Int. Cl.
*A61F 9/007* (2006.01)
*A61F 9/00* (2006.01)
*A61B 17/34* (2006.01)

(52) U.S. Cl.
CPC .......... *A61F 9/007* (2013.01); *A61F 9/00736* (2013.01); *A61B 17/3421* (2013.01); *A61B 17/3462* (2013.01); *A61F 9/0017* (2013.01)

(58) Field of Classification Search
CPC .... A61F 9/007; A61F 9/00736; A61F 9/0017; A61B 17/3462; A61B 17/3421;
(Continued)

(56) References Cited

U.S. PATENT DOCUMENTS 7,846,134 B1 12/2010 Nadolski
2005/0101984 A1* 5/2005 Chanduszko ...... A61B 17/0057
606/185

(Continued)

FOREIGN PATENT DOCUMENTS

JP 2007510458 A 4/2007
JP 2007530137 A 11/2007
(Continued)

OTHER PUBLICATIONS

International Search Report (ISR) for Application No. PCT/JP2016/085359 dated Jan. 10, 2017.
(Continued)

*Primary Examiner* — Bhisma Mehta
*Assistant Examiner* — Daniel Moore
(74) *Attorney, Agent, or Firm* — Isshiki International Law Office; Joseph P. Farrar, Esq.

(57) ABSTRACT

There is provided a piercing needle-equipped cannula that has a pre-attached piercing needle, and no deformation of the slit portion due to the piercing needle is left after the piercing needle is pulled out. A piercing needle-equipped cannula (100) includes: a cannula (10) pierced in an eyeball and used in ophthalmic operations; a resin cap (13) having a slit (13a) opened in the cannula (10); and a piercing needle (15) attached to the cannula (10). The piercing needle (15) includes a needle main body (15c) on a front end side, a base (15d) on a base end side, and a slit piercing part (15s) piercing the slit (13a) in a state where the needle main body (15c) and the base (15d) are connected, and the cross-sectional area of the slit piercing part (15s) is smaller than that of the thickest part of the needle main body (15c).

2 Claims, 4 Drawing Sheets

(58) Field of Classification Search
CPC ........ A61B 17/3417; A61B 2017/3484; A61B 2017/3433
See application file for complete search history.

(56) References Cited

U.S. PATENT DOCUMENTS

| | | |
|---|---|---|
| 2005/0216028 A1 | 9/2005 | Hart et al. |
| 2010/0106177 A1 | 4/2010 | Chanduszko et al. |
| 2011/0152774 A1* | 6/2011 | Lopez .................... A61F 9/007 604/165.04 |
| 2012/0179188 A1 | 7/2012 | Chanduszko et al. |
| 2012/0302961 A1 | 11/2012 | Lopez |
| 2015/0038794 A1* | 2/2015 | Pattison ............. A61B 17/3415 600/204 |
| 2015/0080644 A1* | 3/2015 | Kawaura ............... A61F 2/0045 600/30 |

FOREIGN PATENT DOCUMENTS

| | | |
|---|---|---|
| JP | 2013515563 A | 5/2013 |
| WO | 2010126076 A1 | 11/2010 |

OTHER PUBLICATIONS

Translation of the ISR for Application No. PCT/JP2016/085359 dated Jan. 10, 2017.
Written Opinion of the International Search Authority for Application No. PCT/JP2016/085359 dated Jan. 10, 2017.

* cited by examiner

PIERCING NEEDLE-EQUIPPED CANNULA

CROSS-REFERENCE TO RELATED APPLICATIONS

The present application is a national phase entry under 35 U.S.C. § 371 of International Application No. PCT/JP2016/085359, filed Nov. 29, 2016, which in turn claims priority from Japanese Patent Application No. 2015-234105 filed Nov. 30, 2015, the entire disclosures of which are hereby incorporated by reference herein.

BACKGROUND

Technical Field

The present invention relates to a piercing needle-equipped cannula having a piercing needle pre-attached to a cannula used in ophthalmic operations.

Background Art

The cannula is attached to an eyeball, and a surgical tool or the like is passed through the cannula and used in an ophthalmic operation (e.g., Patent Document 1). FIG. 5 is a cross-section of a typical cannula. A cannula 110 is configured by fitting the base end part of a metal pipe 111 into a base 112 made of resin, and covering and enveloping a side surface of the base 112 and the base end of the pipe 111 by a cap 113 made of resin such as silicone rubber.

The base 112 has a function of a stopper by touching the surface of an eyeball when the pipe 111 is pierced in, and the cap 113 has a function of controlling leakage of vitreous humor etc. from the inside of the eyeball via the pipe 111.

The cap 113 has a slit 113a, which connects the inner side of the pipe 111 and the outer side of the cap 113, provided in a portion that covers a base end of the pipe 111, and various surgical tools, optical instruments for monitoring etc. are then inserted in the eyeball through the slit 113a. Therefore, it is preferable that there is no space between the slit and the surgical tool etc. so that vitreous humor etc. does not leak when using the surgical tool etc.

On the other hand, when attaching such a cannula to an eyeball, a piercing needle is attached to the cannula and set in a holder that acts as a handle. FIG. 6 is diagram illustrating a state where a piercing needle and a cannula are pierced into an eyeball. The cannula 110 is attached to an eyeball A in the steps of attaching the point of the piercing needle 115 so as to protrude from the pipe 111 of the cannula 110, piercing the eyeball A with the piercing needle 115 and the pipe 111 in one united body, and pulling out only the piercing needle 115, leaving only the cannula 110 in the eyeball A. At this time, while the piercing needle 115 should be attached to the cannula 110 in advance to save time, this results in deformation of the slit 113a due to the piercing needle 115 when pulling it out. That is, problems may occur where once the piercing needle 115 is pulled out, the slit 113a is not closed tightly, and a gap generates between the slit 113a and the surgical tool etc. at the time of inserting the surgical tool etc., thereby making it easy for the vitreous humor etc. to leak.

PRIOR ART DOCUMENTS

Patent Documents

[Patent Document 1] WO 2010/126076A

BRIEF SUMMARY

Problem to be Solved

In light of the problem, the present invention aims to provide a piercing needle-equipped cannula that has a piercing needle pre-attached to the cannula, wherein no deformation of the slit portion due to the piercing needle is left after the piercing needle is pulled out.

Solution to the Problem

A piercing needle-equipped cannula according to the present invention is characterized by including; a cannula pierced in an eyeball and used in ophthalmic operations; a resin cap having a slit opened in the cannula; and a piercing needle attached to the cannula. The piercing needle includes a needle main body on a front end side, a base on a base end side, and a slit piercing part piercing the slit in a state where the needle main body and the base are connected, and the cross-sectional area of the slit piercing part is smaller than that of the thickest part of the needle main body.

Here, the material of the slit piercing part may be different from that of the needle main body, or the slit piercing part may be made of a flexible, extremely thin material. Moreover, the cross-sectional shape of the slit piercing part may be a circle or a flat rectangle. Alternatively, the slit piercing part and the base may have the same cross-sectional shape. Further alternatively, the slit may have a linear shape when viewed from the direction of inserting the piercing needle, a curved shape including a crescent, or a shape made up of multiple lines.

Advantageous Effect

According to the present invention, as a result of making the opening of the slit small when attaching the piercing needle to the cannula, there are beneficial effects of no remaining deformation of the slit portion due to the piercing needle after the piercing needle is pulled out, and thus the slit may be closed tightly.

DESCRIPTION OF EMBODIMENTS

An embodiment according to the present invention is described below with reference to accompanying drawings.

Figure 1:
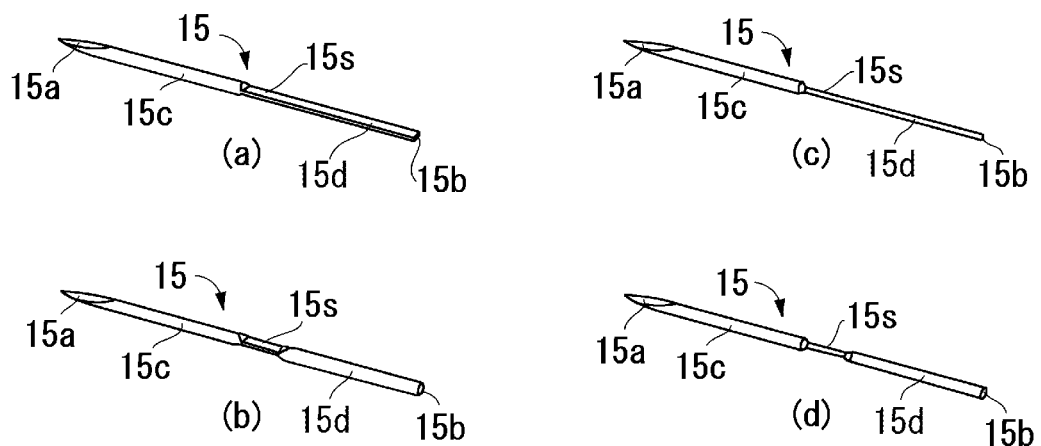
FIG. 1 illustrates four types of piercing needles used for a piercing needle-equipped cannula of the present invention.

FIG. 1 illustrates four types of piercing needles used for a piercing needle-equipped cannula of the present invention. Here, a pointed end part of a piercing needle 15 is a front end 15a, and a pointed end part on the opposite side is a base end 15b.

The basic form of the piercing needle 15 includes a needle main body 15c, which is made from the front end 15a pointed to pierce an eyeball and a cylindrical portion connecting to the front end 15a, a slit piercing part 15s, which is a portion passing through the slit when the cannula is attached and connecting to the needle main body 15c, and a base 15d, which is further on the base end 15b side than the slit piercing part 15s. That is, the slit piercing part 15s is a portion connecting the needle main body 15c and the base 15d.

FIG. 1(a) illustrates a needle having a flatter rectangular cross-sectional shape on the base end 15b side than the slit piercing part 15s, and FIG. 1(b) illustrates a needle having a flat rectangular cross-sectional shape only near the slit piercing part 15s. FIG. 1(c) illustrates a needle having a round cross-sectional shape smaller in diameter on the base end 15b side from the slit piercing part 15s than the diameter of the thickest part of the needle main body 15c, and FIG. 1(d) illustrates a needle having a round cross-sectional shape smaller in diameter only near the slit piercing part 15s than the diameter of the thickest part of the needle main body 15c. In other words, the cross-sectional shapes of the slit piercing part 15s and the base end 15d in FIG. 1(a) and FIG. 1(c) are the same.

If the cross-sectional shape of the slit piercing part 15s is a flat rectangle as in FIGS. 1(a) and 1(b), the opening of the slit can be kept small when the piercing needle 15 is attached to the cannula. Moreover, since deformation of the slit can be kept to a minimum even if the shape is a circle with a small diameter as in FIGS. 1(c) and 1(d), there is hardly any deformation of the slit left after the piercing needle 15 is pulled out.

Note that the cross-sectional shape of the slit piercing part 15s is not limited to a flat rectangle or small circle as illustrated in FIG. 1, basically as long as the cross-sectional area is smaller than the thickest part or columnar portion of the needle main body 15c of the piercing needle 15. This is because if the cross-sectional area is made small, regardless of cross-sectional shape, there is a specific angle at which the height of the cross-sectional area is lower than at least the diameter of the columnar portion of the needle main body 15c, and thus if the piercing needle 15 pierces at such an angle that the opening of the slit is small, there can at least be little deformation of the slit. The slit 13a may have a linear shape when viewed from the direction of inserting the piercing needle, a curved shape including an arc, or a shape made up of multiple lines.

Figure 2:
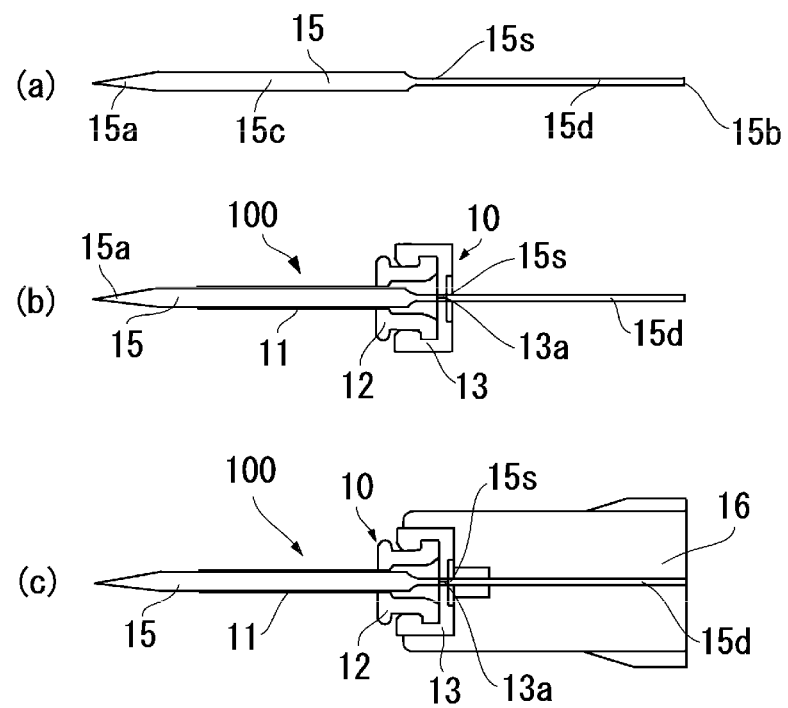
FIG. 2 shows illustrations of the piercing needle-equipped cannula, wherein (a) is a cross-section of the piercing needle, (b) is a cross-section of the piercing needle-equipped cannula, and (c) is a cross-section of the cannula set in a holder.
Figure 3:
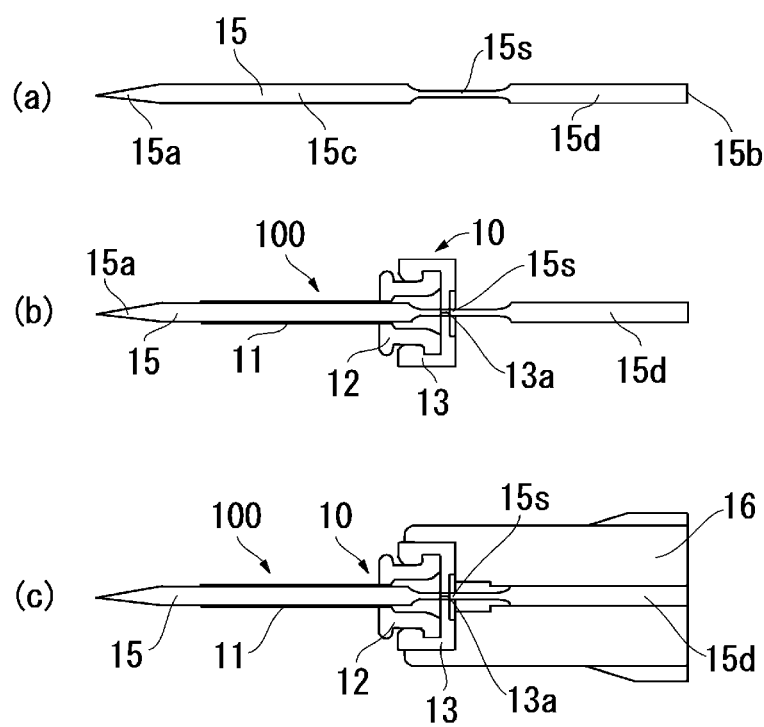
FIG. 3 shows illustrations of a different piercing needle-equipped cannula, wherein (a) is a cross-section of the piercing needle, (b) is a cross-section of the piercing needle-equipped cannula, and (c) is a cross-section of the cannula set in a holder.

FIG. 2 shows illustrations of the piercing needle-equipped cannula/device, wherein FIG. 2(a) is a cross-section of the piercing needle, FIG. 2(b) is a cross-section of the piercing needle-equipped cannula, and FIG. 2(c) is a cross-section of the cannula set in a holder. FIG. 3 shows illustrations of a different piercing needle-equipped cannula, wherein FIG. 3(a) is a cross-section of the piercing needle, FIG. 3(b) is a cross-section of the piercing needle-equipped cannula, and FIG. 3(c) is a cross-section of the cannula set in a holder. FIG. 2 shows where the cross-sectional shape further on the base end 15b side than the slit piercing part 15s is made smaller in accordance with the cross-sectional shape of the slit piercing part 15s, and FIG. 3 shows where the cross-sectional shape only in the vicinity of the slit piercing part 15s is made smaller. Note that FIGS. 1(a) and 1(c), and FIGS. 1(b) and 1(d) have nearly the same shapes when comparing only the respective cross-sectional shapes along the axis of the piercing needle 15, where FIGS. 1(a) and 1(c) are considered to correspond to FIG. 2, and FIGS. 1(b) and 1(d) are considered to correspond to FIG. 3.

The cannula 10 illustrated in FIGS. 2 and 3 has a typical structure in which a base end part of a metal pipe 11 is fit into a resin base 12, covering and enveloping a side surface of the base 12 and the base end of the pipe 11 by a cap 13 made of silicone rubber.

When attaching the piercing needle 15 to the cannula 10, the slit piercing part 15s is attached so as to be positioned at the slit 13a opened in the cap 13, and at that time, a pointed front end 15a of the piercing needle 15 protrudes out from the pipe 11 of the cannula 10. Note that by making the outer diameter of the cylindrical portion of the needle main body 15c almost the same as the inner diameter of the pipe 11, rattling between the piercing needle 15 and a cannula 100 is suppressed.

Moreover, when attaching the cannula 10 to the eyeball, the piercing needle-equipped cannula 100 is secured by a holder 16 acting as a handle. The holder 16 secures the base 15d and the periphery of the cap 13, which is attached to the cannula 10. Note that since the cross-sectional shape of the base 15d is different in FIGS. 2 and 3, places near the base 15d secured by the holder 16 are appropriate for the cross-sectional shapes of the respective bases 15d.

As shown in FIGS. 2(c) and 3(c), the piercing needle 15 and the pipe 11 of the cannula 10 are pierced into the eyeball with the holder 16 having secured them. Only the piercing needle 15 is pulled out while leaving the cannula 10 therewithin, thereby attaching the cannula 10 to the eyeball. If the piercing needle-equipped cannula 100 of the present invention is used at this time, after the piercing needle 15 is pulled out, no deformation of the slit 13a due to the piercing needle 15 is left, making the slit 13a tightly closed. This allows suppression of vitreous humor etc. from leaking out of the eyeball, and performance of a safe ophthalmic operation.

Figure 4:
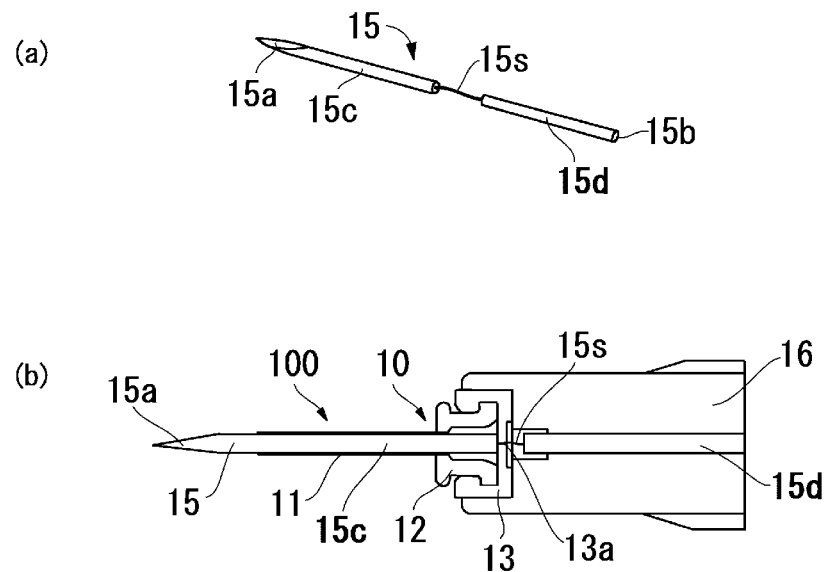
FIG. 4 shows illustrations of a different piercing needle-equipped cannula, wherein (a) is an oblique view of the piercing needle, and (b) is a cross-section of the cannula set in a holder.
Figure 5:
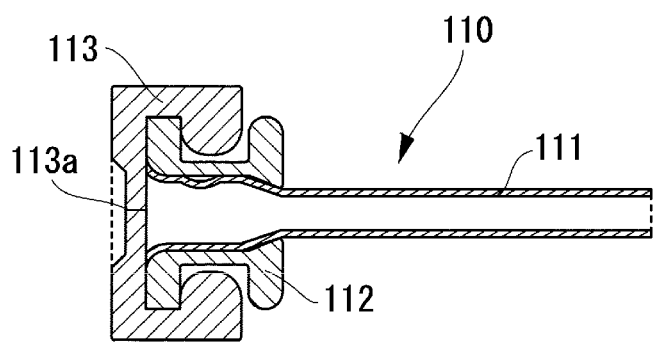
FIG. 5 is a cross-section of a typical cannula.
Figure 6:
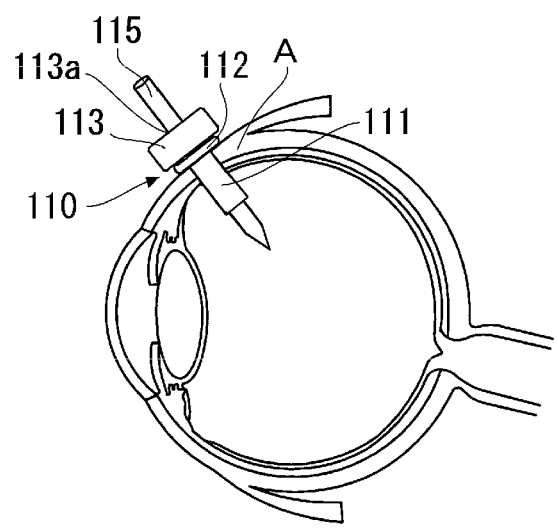
FIG. 6 is a diagram illustrating a state where a piercing needle and a cannula are pierced into an eyeball.

FIG. 4 shows illustrations of a different piercing needle-equipped cannula, wherein FIG. 4(a) is an oblique view of the piercing needle, and FIG. 4(b) is a cross-section of the cannula set in a holder. The piercing needle 15 illustrated here includes the needle main body 15c on the front end 15a side, the base 15d on the base end 15b side, and the slit piercing part 15s connecting the needle main body 15c and the base end 15b.

In this case, since the piercing needle 15 illustrated in FIG. 1 is manufactured as one body, all parts are made from the same material (e.g., austenitic stainless steel, etc.). On the other hand, the piercing needle 15 illustrated in FIG. 4(a) has the slit piercing part 15s made of a flexible, extremely thin material. That is, the needle main body 15c is made of a different material from that of the slit piercing part 15s. Moreover, if the slit piercing part 15s is very thin, there is a beneficial effect of no remaining deformation of the slit portion due to the piercing needle. Note that the flexible, extremely thin material corresponds to thread, string, wire etc., but is not limited thereto.

Furthermore, the base 15d may also be made of a different material than that of the needle main body 15c. This is because while the needle main body 15c needs to be made of a material (e.g., austenitic stainless steel, etc.) such as that used for a conventional piercing needle, so as for the needle main body to pierce the eyeball, securing it by the holder 16 is sufficient as the base 15d itself does not pierce the eyeball. Note that the slit piercing part 15s and the base 15d are made of different materials and have different cross-sectional shapes in FIG. 4; however, alternatively, they may be made of the same material and have the same cross-sectional shape as in FIGS. 1(a) and 1(c). In this case where the base 15d and the slit piercing part 15s are made of the same flexible, extremely thin material, a configuration in which the end part of the base 15d is secured to the inner side of the holder 16 is possible. However, the method of securing the base 15d by the holder 16 is not limited.

FIG. 4(b) illustrates the cannula set in the holder 16. The piercing needle-equipped cannula 100 should be stable when piercing the eyeball in this state. Moreover, since the piercing needle 15 needs to be pulled out after piercing, connections between the needle main body 15c and the slit piercing part 15s and between the slit piercing part 15s and the base 15d require strengthening so as not to detach. As long as the above conditions are fulfilled, the piercing needle 15 may have the structure as in FIG. 4(a) without any problems, and there is a beneficial effect of no remaining deformation of the slit portion due to the piercing needle.

EXPLANATION OF REFERENCES

10: Cannula
11: Pipe
12: Base
13: Cap
13a: Slit
15: Piercing needle
15a: Front end
15b: Base end
15c: Needle main body
15d: Base
15s: Slit piercing part
16: Holder
100: piercing needle-equipped cannula/device
A: Eyeball

The invention claimed is:

1. A piercing needle-equipped device, comprising:
a cannula adapted to pierce an eyeball and used in ophthalmic operations;
a resin cap having a slit that can be opened in the cannula; and
a piercing needle attached to the cannula, wherein
the piercing needle is comprised of a needle main body on a front end side, a base on a base end side, and a slit piercing part connecting the needle main body and the base wherein the slit piercing part pierces the slit,
a cross-sectional area of the slit piercing part is smaller than a cross-sectional area of a thickest part of the needle main body, and
a cross-sectional shape of the slit piercing part is a flat rectangle.

2. The piercing needle-equipped device of claim 1, wherein the slit piercing part and the base have the same cross-sectional shape.

* * * * *